US00PP16260P2

(12) United States Plant Patent
Bennerup

(10) Patent No.: US PP16,260 P2
(45) Date of Patent: Feb. 14, 2006

(54) BASIL PLANT NAMED 'PESTO PERPETUO'

(50) Latin Name: *Ocimum×citriodorum*
Varietal Denomination: Pesto Perpetuo

(75) Inventor: Pierre Bennerup, Berlin, CT (US)

(73) Assignee: Sunny Border Nurseries, Inc., Kensington, CT (US)

( * ) Notice: Subject to any disclaimer, the term of this patent is extended or adjusted under 35 U.S.C. 154(b) by 60 days.

(21) Appl. No.: 10/989,920

(22) Filed: Nov. 8, 2004

(51) Int. Cl.
*A01H 5/00* (2006.01)

(52) U.S. Cl. ..... Plt./258
(58) Field of Classification Search ..... Plt./258
See application file for complete search history.

*Primary Examiner*—Anne Marie Grunberg
(74) *Attorney, Agent, or Firm*—Penny J. Aguirre

(57) ABSTRACT

A new cultivar of Greek columnar basil for landscape and culinary use, *Ocimum×citriodorum* 'Pesto Perpetuo', characterized by variegated foliage of green centers and white margins and its non-flowering habit enabling year around vegetative propagation.

1 Drawing Sheet

Botanical classification: *Ocimum×citriodorum.*
Varietal denomination: 'Pesto Perpetuo'.

BACKGROUND OF THE INVENTION

The present invention relates to a new and distinct cultivar of *Ocimum×citriodorum* and will be referred to hereafter by its cultivar name, 'Pesto Perpetuo'. 'Pesto Perpetuo' represents a new cultivar of Greek columnar basal, a tender perennial grown for landscape and culinary use.

The inventor discovered the new cultivar, 'Pesto Perpetuo', in a block of containers of *Ocimum×citriodorum* 'Lesbos' (not patented) in his nursery in Kensington, Conn. in April of 2004. 'Pesto Perpetuo' arose as a naturally occurring branch sport of 'Lesbos'.

The new cultivar was selected as unique for its variegated foliage characterized by leaves with green centers and white margins. The parent plant, 'Lesbo' is non-variegated. 'Pesto Perpetuo' is non-flowering, a characteristic that it has in common with 'Lesbos'.

Asexual reproduction of the new cultivar was first accomplished by terminal stem cuttings in Kensington, Conn. in May of 2004 by the inventor. The characteristics of this cultivar have been determined to be stable and are reproduced true to type in successive generations.

SUMMARY OF THE INVENTION

The following traits have been repeatedly observed and represent the characteristics of the new cultivar as observed on plants grown in an outdoor trial plot for one growing season in Kensington, Conn. These attributes in combination distinguish 'Pesto Perpetuo' from other Basil varieties known to the inventor.

1. 'Pesto Perpetuo' exhibits variegated foliage with leaves having green centers and white margins. The parent plant, 'Lesbos' is non-variegated.
2. 'Pesto Perpetuo' is non-flowering, similar to the parent plant.
3. 'Pesto Perpetuo' remains vegetative, propagation by terminal stem cuttings is possible 12 months a year.

BRIEF DESCRIPTION OF THE DRAWING

The accompanying color photograph illustrated the foliage characteristics of a four month-old plant of 'Pesto Perpetuo' as grown in a one-quart container in a greenhouse in Kensington, Conn. The colors in the photographs are as close as possible with the digital photography techniques available, the color values cited in the detailed botanical description accurately describe the colors of the new Basil.

DETAILED BOTANICAL DESCRIPTION

The following is a detailed description of the new cultivar as grown outdoors and in a greenhouse for an entire growing season in Kensington, Conn. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

Botanical classification: 'Pesto Perpetuo' is a cultivar of *Ocimum×citriodorum.*
Common name: Pesto Perpetuo Green columnar basil.
Parentage: Naturally occurring branch sport of *Ocimum× citriodorum 'Lesbo'.*
General description:
- *Plant habit.*—Tender perennial, clump forming, upright, non-flowering.
- *Growth rate.*—Moderately vigorous.
- *Height and spread.*—Reaches about 1 to 1.25 m (3 to 4 ft) in height, about 60 cm (2 ft) in width in a normal growing season in Kensington, Conn.
- *Culture.*—Prefers full sun and humus rich soils, in average temperatures above 50° F.
- *Diseases and pests.*—No disease resistance studies have been performed for 'Pesto Perpetuo'.
- *Root description.*—Fibrous and fine.

Growth and propagation:
- *Propagation.*—Terminal stem cuttings, possible 12 months a year as the plants remain vegetative.

*Root initiation and development.*—Cuttings root in 2 to 3 weeks, rooted cuttings fully develop a 72-cell plug in 4 to 6 weeks when grown in soil-less media in a greenhouse conditions with bottom heat and an air temperature of 68° F.

Stem description:

*Stem shape.*—Round when young, becoming more square with age.

*Stem color.*—Intermediate color between 144A and 144B, older stems are tinged with N79A.

*Stem size.*—Up to 1 cm in diameter, main stem is up to about 1.2 m in length.

*Stem surface.*—Glabrous.

*Internode length.*—Up to 4 cm.

*Branching.*—About 3 to 4 secondary branches per main stem.

Foliage description:

*Leaf arrangement.*—Opposite with secondary set of leaves developing at nodes after primary leaves expand.

*Leaf shape.*—Ovate to Elliptic.

*Leaf division.*—Simple.

*Leaf base.*—Cuneate.

*Leaf apex.*—Acute.

*Leaf venation.*—Pinnate, not conspicuous, color on upper surface is the same as the leaf color, color on lower surface 139D with glistening appearance.

*Leaf margins.*—Serrate.

*Leaf attachment.*—Petiolate.

*Leaf surface.*—Upper and lower surfaces: glabrous with lower surface also appearing glandular.

*Leaf color.*—Immature: upper and lower surface; centers between 138B and 138C, margins 155A. Mature: upper; centers 138B, margins 155B, lower; centers 138C, margins 155B.

*Leaf size.*—Average of 4 cm length and 2.5 cm in width.

*Leaf fragrance.*—Strongly basil-scented.

*Petiole size.*—Average of 1 cm in length and 2.5 mm in width.

*Petiole color.*—Intermediate color between 144A and 144B.

Flower description: 'Pesto Perpetuo' is non-flowering.

I claim:

1. A new and distinct cultivar of Basil plant named 'Pesto Perpetuo' as herein illustrated and described.

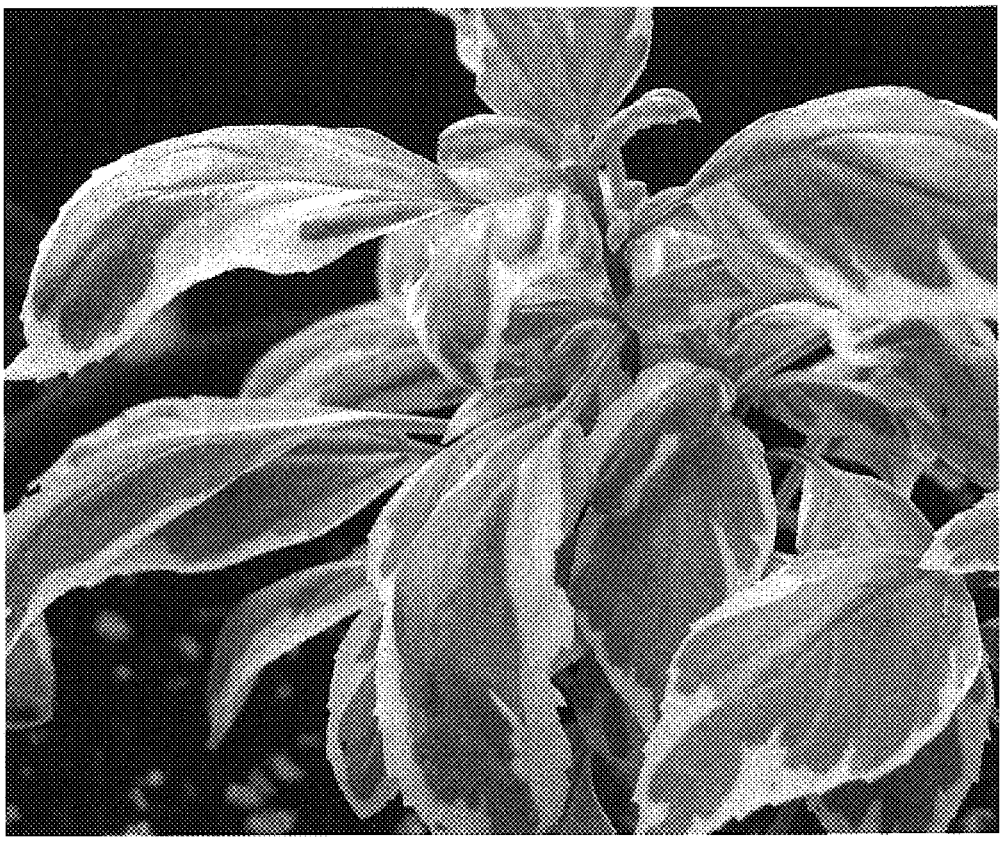

* * * * *